United States Patent [19]

Hirth

[11] Patent Number: 4,588,943
[45] Date of Patent: May 13, 1986

[54] INSTRUMENT FOR MEASURING THE MOISTURE CONTENT OF DIELECTRIC OBJECTS

[75] Inventor: Friedrich Hirth, Stuttgart, Fed. Rep. of Germany

[73] Assignee: Gann Mess-u. Regeltechnik GmbH, Stuttgart, Fed. Rep. of Germany

[21] Appl. No.: 597,360

[22] Filed: Apr. 6, 1984

[30] Foreign Application Priority Data

Aug. 31, 1983 [DE] Fed. Rep. of Germany ....... 3331305

[51] Int. Cl.⁴ .............................................. G01R 27/26
[52] U.S. Cl. .................................................. 324/61 P
[58] Field of Search ............ 324/61 P, 61 QL, 61 QS, 324/61 R

[56] References Cited

U.S. PATENT DOCUMENTS

| | | | |
|---|---|---|---|
| 2,428,700 | 10/1947 | Eilenberger | 324/61 R |
| 3,559,052 | 1/1971 | Fathauer | 324/61 R |
| 3,609,735 | 9/1971 | Dauterman | 324/61 R X |
| 3,651,505 | 3/1972 | Schmidt | 324/61 R X |
| 3,714,560 | 1/1973 | Farr | 324/61 R |
| 3,879,644 | 4/1975 | Maltby | 324/61 P X |

Primary Examiner—Stanley T. Krawczewicz
Attorney, Agent, or Firm—Peter K. Kontler

[57] ABSTRACT

An instrument for measuring the moisture content of dielectric objects has a housing which supports capacitance measuring means. The capacitance measuring means includes a circuit which is connected with a high frequency voltage source and is designed to measure changes in capacitance. The capacitance measuring means further includes an electrically conductive rod which projects from the housing and carries an active electrode at the end thereof remote from the housing. The active electrode is connected with one terminal of the circuit and is designed to generate a diverging voltage field which penetrates into an object undergoing moisture determination. The capacitance measuring means is devoid of an electrode which is capable of cooperating with the active electrode to generate signals during moisture determination. Instead, the second terminal of the circuit is connected with a metallic cover plate which forms part of the housing and constitutes a ground of the latter. The cover plate is designed to be contacted by an operator and thus grounded during moisture determination.

15 Claims, 3 Drawing Figures

PRIOR ART

INSTRUMENT FOR MEASURING THE MOISTURE CONTENT OF DIELECTRIC OBJECTS

BACKGROUND OF THE INVENTION

The invention relates generally to an instrument for measuring moisture content.

More particularly, the invention relates to an instrument for measuring the moisture content of dielectric substances, especially dielectric solids.

A known instrument for measuring the moisture content of dielectric objects has a housing which accommodates a measuring circuit designed to detect small changes in capacitance. A measuring capacitor capable of generating a diverging voltage field extends from the housing.

The measuring capacitor in a conventional instrument of this type consists of a plurality of parallel or concentric electrodes. The electrode arrangement includes both active and grounded electrodes and is designed in such a manner that the active electrodes alternate with or are located adjacent to the grounded electrodes. In other words, each active electrode is located between two grounded electrodes.

In order to determine the moisture content of an object, the electrodes are placed against the object. Conventional instruments of the type under consideration are designed on the assumption that the spacing between the electrodes must be smaller than the dimensions of the object. It is believed that virtually the entire voltage field of the measuring capacitor then penetrates into the object.

In these moisture measuring instruments, the depth of penetration of the voltage field into the object is highly unsatisfactory. Thus, the field strength decreases significantly within a few millimeters. This results in substantial errors when, as is the case for many solids, the moisture distribution in an object is very non-uniform. For example, structural components consisting of synthetic resins may exhibit a non-uniform moisture distribution when used under extreme conditions since they may develop hairline cracks or pores which can trap water. If a moisture determination on such a structural component is made at an inner surface thereof, any moisture which may, for instance, have accumulated in hairline cracks at the outer surface cannot be detected. The same applies, for example, to moisture determinations performed on wood where a non-uniform moisture distribution along the thickness develops during drying.

OBJECTS AND SUMMARY OF THE INVENTION

It is an object of the invention to provide an instrument which is capable of measuring the moisture content of dielectric substances more accurately than heretofore.

Another object of the invention is to provide an instrument of the type outlined above which is particularly well-suited for determining the moisture content of dielectric solids and is capable of detecting moisture at greater depths than conventional instruments.

The preceding objects, as well as others which will become apparent as the description proceeds, are achieved by the invention.

One aspect of the invention resides in an instrument for measuring moisture content which comprises support means, and capacitance measuring means mounted on the support means. The capacitance measuring means includes a capacitance measuring circuit having first and second terminals for connection with respective electrodes which cooperate to cause the generation of measuring signals during moisture determination. The capacitance measuring means further includes an active first electrode which is connected with the first terminal. The capacitance measuring means is devoid of a cooperating electrode for the first electrode and the second terminal is designed for connection with ground which constitutes a second electrode during moisture determination and cooperates with the first electrode to cause the generation of measuring signals.

The support means may comprise a housing for the capacitance measuring circuit. The latter is preferably designed so as to be capable of detecting small changes in capacitance.

The first or active electrode may constitute or form part of a measuring capacitor. The measuring capacitor is favorably designed so that a diverging voltage field may be generated at or in the region of the active electrode.

The capacitance measuring means preferably projects from the support means. The active electrode may here be located at the end of the capacitance measuring means remote from the support means.

In the capacitance measuring means of the invention, an active electrode is physically present while a grounded electrode for cooperation with the active electrode is absent. An instrument according to the invention for measuring the moisture content of dielectric substances enables a diverging voltage field of maximum size and maximum depth of penetration to be generated. This makes it possible to measure the moisture content of a body having a very non-uniform moisture distribution more accurately than heretofore.

The moisture measuring instrument of the invention is particularly well-suited for determining the moisture content of a solid dielectric object.

It is of advantage for the active electrode to be small as compared to the object undergoing moisture determination. This further increases the depth of penetration of the diverging voltage field used for measurement of the moisture content.

According to one embodiment of the invention, the capacitance measuring means includes an elongated, electrically conductive member having a first end which is secured to and a second end which is remote from the support means. The active electrode is mounted at the latter end of the elongated member. The elongated member is preferably in the form of a metallic, rod-like element. This embodiment makes the instrument easier to handle and permits the instrument to be used in a tilted or inclined position.

Advantageously, the active electrode is spherical or semispherical or resembles a spherical calotte.

The novel features which are considered as characteristic of the invention are set forth in particular in the appended claims. The improved instrument itself, however, both as to its construction and its mode of operation, together with additional features and advantages thereof, will be best understood upon perusal of the following detailed description of certain specific embodiments with reference to the accompanying drawings.

DESCRIPTION OF THE PREFERRED EMBODIMENTS

Figure 1:
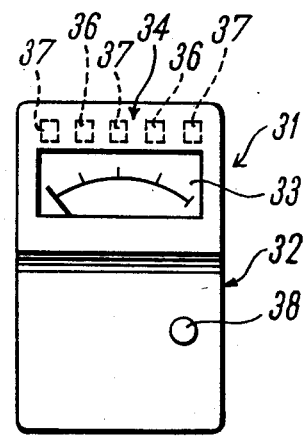
FIG. 1 is a schematic plan view of a prior art instrument designed to measure the moisture content of dielectric objects and having a cone-like electrode arrangement.

Referring to FIG. 1, the reference numeral 31 identifies an instrument according to the prior art for measuring the moisture content of dielectric objects. The instrument 31 has a housing 32 which accommodates a non-illustrated measuring circuit. The measuring circuit is connected with a non-illustrated high frequency voltage generator as well as with an indicator 33 located at the front of the instrument 31. The measuring circuit is further connected with a measuring capacitor arrangement 34 which is designed to generate a diverging voltage field and is disposed at the back of the instrument 31.

The measuring capacitor arrangement 34 comprises two active electrodes 36 which are connected with one terminal of the measuring circuit. The measuring capacitor arrangement 34 further includes three additional electrodes 37 which are connected with the other terminal of the measuring circuit and are grounded. Each of the active electrodes 36 is located between two cooperating grounded electrodes 37.

During measurement of the moisture content of an object, the electrodes 36 and 37 are placed against the object. The spacing between the electrodes 36 and 37 is smaller than the thickness of the object.

A knob 38 is provided to activate the instrument 31.

Figure 2:
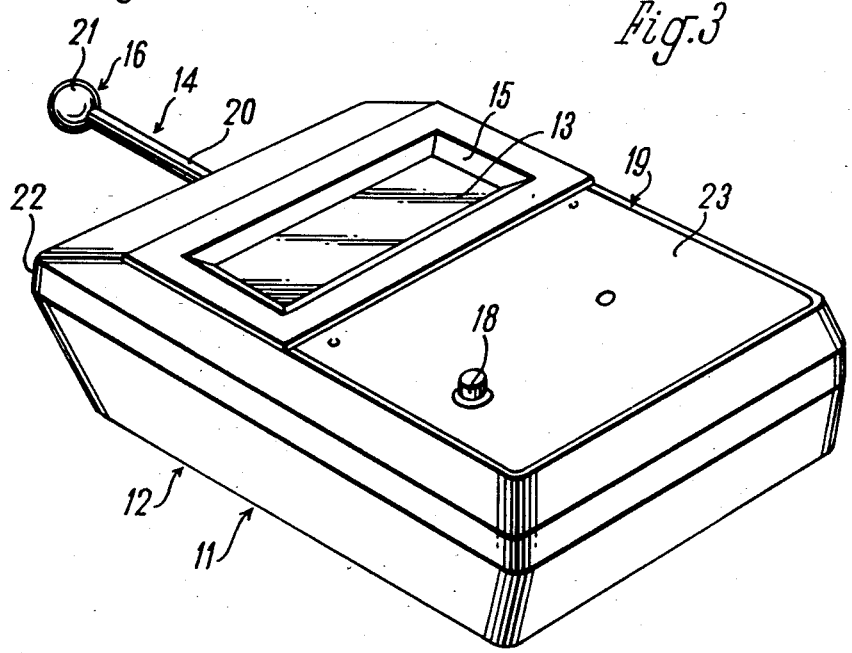
FIG. 2 is a schematic perspective view of an instrument according to the invention for measuring the moisture content of dielectric substances.

FIG. 2 illustrates an instrument 11 according to the invention for measuring the moisture content of dielectric substances. The instrument 11 is particularly well-suited for measuring the moisture content of dielectric solids.

Figure 3:
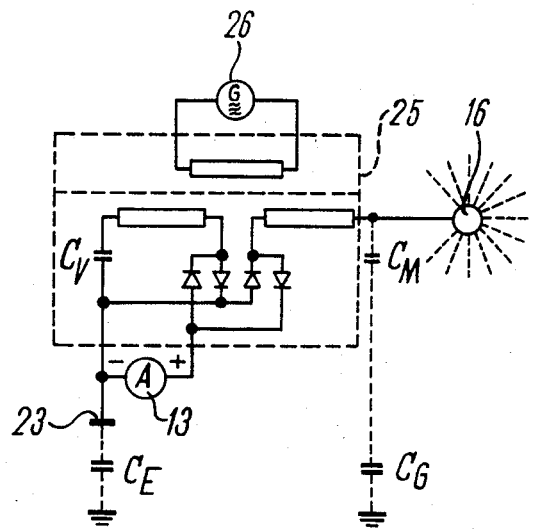
FIG. 3 schematically illustrates a measuring circuit for the instrument of FIG. 2.

The instrument 11 includes a housing or support means 12 which carries capacitance measuring means. The capacitance measuring means includes a measuring capacitor arrangement 14 which is designed to generate a diverging voltage field for measuring purposes. The capacitance measuring means further comprises a conventional measuring circuit 25 which is schematically illustrated in FIG. 3. As also shown in FIG. 3, the measuring circuit 25 is connected with a high frequency voltage source 26. The measuring circuit 25 is accommodated inside the housing 12. The measuring circuit 25 is connected with and is designed to detect small capacitance variations in the measuring capacitor arrangement 14.

The housing 12 has a front wall 19 which is provided with a cutout for window 15. An indicator 13 is mounted on the housing 12 behind the window 15 and is visible through the latter. As illustrated in FIG. 3, the indicator 13 is connected with the measuring circuit 25 so that the indicator 13 may indicate capacitance changes which occur in the measuring capacitor arrangement 14.

The housing 12 has a lateral wall 22. The measuring capacitor arrangement 14 includes an electrically conductive rod 20 which projects from the housing 12 and is mechanically secured to the lateral wall 22. The rod 20, which is preferably metallic, is normal to the lateral wall 22.

The measuring capacitor arrangement 14 further includes a capacitor having an active electrode 16. The electrode 16 comprises or is constituted by a spherical calotte or sphere 21 composed of metal. The sphere 21 is mounted at the end of the rod 20 remote from the housing 12.

As may be seen in FIG. 3, the active electrode 16 is electrically connected with one terminal of the measuring circuit 25 or voltage source 26. FIG. 3 also shows by phantom lines radiation from the active electrode 16 that the latter is designed to generate a diverging voltage field for measuring purposes.

The length of the rod 20 is selected in such a manner that a slight inclination of the instrument 11 suffices to bring the electrode 16 into contact with an object to undergo moisture determination. The electrode 16 is dimensioned so as to be small relative to an object which is to have its moisture content determined.

The capacitance measuring means 14,25 is devoid of a cooperating electrode for the active electrode 16, that is, the capacitance measuring means 14,25 does not have an electrode which acts in conjunction with the active electrode 16 to generate signals during moisture determination. Stated differently, a cooperating electrode for the active electrode 16 is not physically or structurally present in the capacitor of the measuring capacitor arrangement 14. Instead, the cooperating electrode for the active electrode 16 is constituted by electrically conductive ground.

As mentioned previously, the electrode 16 is connected with one terminal of the measuring circuit 25. The other terminal of the measuring circuit 25 is electrically connected with a metallic plate 23. The plate 23 forms part of the front wall 19 of the housing 12 and constitutes a ground of the housing 12. The metallic plate 23 is disposed on that side of the window 15 which is remote from the measuring capacitor arrangement 14 and serves as a cover for the measuring circuit 25 inside the housing 12.

A button 18 passes through the cover plate 23 and functions to activate the moisture measuring instrument 11.

FIG. 3 illustrates that the measuring circuit 25 comprises a reference capacitor having a reference capacitance $C_V$. FIG. 3 further illustrates by phantom lines the capacitances which arise during moisture determination. The latter capacitances are represented by equivalent circuit elements.

The capacitance $C_M$ represented by an equivalent circuit element is the measured capacitance of the object undergoing moisture determination. The capacitance $C_E$ represented by an equivalent circuit element is the capacitance generated between the measuring instrument 11 and ground, that is, between ground and an operator who touches the cover plate 23 constituting a ground of the instrument 11. The capacitance $C_G$ represented by an equivalent circuit element is the capacitance generated between ground and the object undergoing moisture determination. It may be assumed that the capacitances $C_E$ and $C_G$ are each substantially larger than $C_M$.

The reference capacitance $C_V$ of the reference capacitor in the measuring circuit 25 equals the capacitance of the air. The dielectric constant is then equal to one and the moisture measuring instrument 11 is balanced.

In operation, the instrument 11 reads zero when it is held in air and the operator touches the metallic cover plate 23 while depressing the button 18. If an object is brought into the diverging voltage field of the active electrode 16 so that the object contacts the electrode 16, the instrument 11 indicates the difference in the dielectric constants of the air and the object. This, in turn, is a measure of the moisture content of the object since the dielectric constant of the object changes with moisture content.

Instead of a single sphere 21, the active electrode 16 of the measuring capacitor may comprise two or more spheres which are arranged at a distance from the housing 12. The different spheres are preferably mounted in such a manner as to be capable of contacting an object undergoing moisture determination simultaneously.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An instrument for measuring moisture content, particularly the moisture content of dielectric solids, comprising support means; and capacitance measuring means mounted on said support means and including a capacitance measuring circuit having first and second terminals for connection with respective electrodes which cooperate to cause the generation of measuring signals during moisture determination, said capacitance measuring means further including an active first electrode which is connected with said first terminal and contacts the object whose moisture content requires determination, and said capacitance measuring means being devoid of a cooperating electrode for said first electrode, said second terminal being designed for connection with ground which constitutes a second electrode during moisture determination and cooperates with said first electrode, without touching the object which is contacted by said first electrode, to cause the generation of measuring signals.

2. The instrument of claim 1, wherein said first electrode at least in part constitutes a measuring capacitor.

3. The instrument of claim 1, wherein said capacitance measuring means is designed to generate a diverging voltage field in the region of said first electrode.

4. The instrument of claim 1, wherein said support means comprises a housing which accommodates said measuring circuit.

5. The instrument of claim 1, wherein said capacitance measuring means projects and has an end remote from said support means, said first electrode being located at said end.

6. The instrument of claim 1, wherein said first electrode is small relative to an object undergoing moisture determination therewith.

7. The instrument of claim 1, wherein said capacitance measuring means comprises an elongated, electrically conductive member having a first end which is secured to and a second end which is remote from said support means, said first electrode being mounted at said second end.

8. The instrument of claim 7, wherein said elongated member is metallic.

9. The instrument of claim 7, wherein said elongated member is rod-like.

10. The instrument of claim 1, wherein said first electrode is substantially spherical.

11. The instrument of claim 1, wherein said first electrode resembles a spherical calotte.

12. The instrument of claim 1, wherein said first electrode is substantially hemispherical.

13. The instrument of claim 1, wherein said support means comprises a metallic portion which is connected with said second terminal and constitutes a grounding portion of said instrument.

14. The instrument of claim 11, wherein said metallic portion comprises a cover for said measuring circuit.

15. The instrument of claim 14, wherein said cover is plate-like.

* * * * *